US012285541B2

(12) United States Patent
Bar-Or et al.

(10) Patent No.: US 12,285,541 B2
(45) Date of Patent: Apr. 29, 2025

(54) PHARMACEUTICAL COMPOSITIONS FOR TREATING OSTEOARTHRITIS

(71) Applicant: INSIGNIA PHARMACEUTICALS, LLC, Wilmington, DE (US)

(72) Inventors: David Bar-Or, Englewood, CO (US); Gregory Thomas, Englewood, CO (US); Melissa Hausburg, Englewood, CO (US); Jason Williams, Englewood, CO (US); Raphael Bar-Or, Englewood, CO (US)

(73) Assignee: INSIGNIA PHARMACEUTICALS, LLC, Wilmington, DE (US)

( * ) Notice: Subject to any disclaimer, the term of this patent is extended or adjusted under 35 U.S.C. 154(b) by 0 days.

(21) Appl. No.: 18/424,626

(22) Filed: Jan. 26, 2024

(65) Prior Publication Data

US 2024/0252715 A1 Aug. 1, 2024

Related U.S. Application Data (60) Provisional application No. 63/509,085, filed on Jun. 20, 2023, provisional application No. 63/441,415, filed on Jan. 26, 2023.

(51) Int. Cl.
*A61L 27/20* (2006.01)
*A61L 27/52* (2006.01)
*A61L 27/54* (2006.01)

(52) U.S. Cl.
CPC .............. *A61L 27/20* (2013.01); *A61L 27/52* (2013.01); *A61L 27/54* (2013.01); *A61L 2300/222* (2013.01); *A61L 2300/412* (2013.01); *A61L 2430/06* (2013.01)

(58) Field of Classification Search
None
See application file for complete search history.

(56) References Cited

U.S. PATENT DOCUMENTS

| | | | |
|---|---|---|---|
| 4,647,453 A | 3/1987 | Meisner | |
| 8,168,669 B2 | 5/2012 | Matsumoto et al. | |
| 9,511,016 B2 | 12/2016 | Oronsky et al. | |
| 9,511,093 B2 | 12/2016 | Gregory et al. | |
| 9,789,062 B2 * | 10/2017 | Hong | A61K 47/28 |
| 9,833,460 B2 * | 12/2017 | Shah | A61K 47/36 |
| 10,500,225 B2 | 12/2019 | Tauzin | |
| 10,543,242 B2 | 1/2020 | Stancioiu et al. | |
| 10,668,118 B2 | 6/2020 | Lynch et al. | |
| 10,668,158 B2 | 6/2020 | Yang et al. | |
| 2007/0208134 A1 | 9/2007 | Hunter et al. | |
| 2012/0321597 A1 | 12/2012 | Hill et al. | |
| 2019/0209446 A1 | 7/2019 | Han et al. | |
| 2020/0281998 A1 | 9/2020 | Scharp et al. | |
| 2021/0095254 A1 | 4/2021 | Frank et al. | |
| 2021/0260010 A1 | 8/2021 | Hamill et al. | |

FOREIGN PATENT DOCUMENTS

| | | |
|---|---|---|
| EP | 1713464 A2 | 10/2006 |
| KR | 10-0420560 B1 | 3/2004 |
| WO | 2005/077356 A3 | 8/2005 |
| WO | 2019/066505 A1 | 4/2019 |

OTHER PUBLICATIONS

Kadir et al., "Evaluation of Chondroprotective Activity of Channa striatus in Rabbit Osteoarthritis Model," BioMed Research International, Jul. 3, 2019, vol. 2019, Article ID 6979585, 11 pages.
Elmaidomy et al., "Anti-Inflammatory and Antioxidant Properties of Malapterurus electricus Skin Fish Methanolic Extract in Arthritic Rats: Therapeutic and Protective Effects," Marine Drugs, Oct. 14, 2022, vol. 20, No. 639, 22 pages.
Isik et al., "Investigation the fatty acid profile of commercial black cumin seed oils and seed oil capsules: Application to real samples", Journal of Chemical Metrology, Oct. 2019, pp. 53-60, vol. 13, No. 2.
Garrett et al., "Long COVID: Is there a kidney link?," Frontiers in Medicine, Apr. 3, 2023, vol. 10, 7 pages.
Hajsl et al., "Tryptophan Metabolism, Inflammation, and Oxidative Stress in Patients with Neurovascular Disease," Metabolites, May 19, 2020, vol. 10, No. 208, 19 pages.
Stone et al., "Modulation of T cells by tryptophan metabolites in the kynurenine pathway," Trends in Pharmacological Sciences, Jul. 2023, pp. 442-456, vol. 44, No. 7.
Nayak et al., "Role of Tryptophan in Health and Disease: Systematic Review of the Anti-Oxidant, Anti-Inflammation, and Nutritional Aspects of Tryptophan and Its Metabolites," World Heart Journal, Sep. 2019, pp. 161-178, vol. 11, No. 2.
"International Search Report and Written Opinion of the International Searching Authority," issued in connection with Int'l Appl. No. PCT/US2024/013250, dated Apr. 16, 2024 (16 pages).
Grecomoro, G. et al.,"Therapeutic synergism between hyaluronic acid and dexamethasone in the intra-articular treatment of osteoarthritis of the knee: a preliminary open study," Current Medical Research and Opinion, vol. 13, Issue. 1, 1992, pp. 49-55.
Zhang et al., "Caprylic acid suppresses inflammation via TLR4/NF-κB signaling and improves atherosclerosis in ApoE-deficient mice", Nutrition & Metabolism, vol. 16, Issue. 40, pp. 1-16.

\* cited by examiner

*Primary Examiner* — Dale R Miller
(74) *Attorney, Agent, or Firm* — Holland & Hart LLP (57) ABSTRACT

The present disclosure provides methods and compositions comprising hyaluronic acid (HA) hydrogel in combination with a saturated fatty acid for treating osteoarthritis. In some embodiments, aspects of the disclosure relate to pharmaceutical compositions comprising HA hydrogel in combination with a steroid. In some embodiments, the pharmaceutical compositions may be administrable via local, topical, and injection. In some embodiments, the pharmaceutical composition may be administrable by intra-articular injection.

12 Claims, 9 Drawing Sheets

… pharmaceutical compositions for treating osteoarthritis …

PHARMACEUTICAL COMPOSITIONS FOR TREATING OSTEOARTHRITIS

CROSS-REFERENCE TO RELATED APPLICATIONS

This patent application claims priority to U.S. Provisional Patent Application No. 63/441,415, filed Jan. 26, 2023, and U.S. Provisional Patent Application No. 63/509,085, filed Jun. 20, 2023, each of which is incorporated by reference in its entirety.

BACKGROUND

Inflammation creates a tremendous global disease burden. Osteoarthritis, for example, affects 25 to 35 million people in the United States alone. Inflammation within the joint cartilage and bone is believed to drive osteoarthritis, which results in chronic pain and disability that gradually worsens with age. Symptomatic osteoarthritis of the knee occurs in over ten percent of persons aged 60 and above, and knee osteoarthritis decreases mobility more than any other medical condition in seniors.

Current pharmaceutical interventions for osteoarthritis are limited to analgesics, non-steroidal anti-inflammatory drugs (NSAIDs), and intra-articular steroid injections, each of which presents limiting or detrimental side effects. In view of these pharmaceutical limitations, chronic osteoarthritis of the knee often results in progressive disability that eventually requires total joint replacement. The increased prevalence of osteoarthritis of the knee in aging and obese populations suggests a growing clinical need for safe and effective pharmaceutical interventions to delay and potentially eliminate the need for orthopedic surgery.

Chronic inflammation and/or osteoarthritis can be treated, for example, with corticosteroids, NSAIDS, and tumor necrosis factor (TNF) inhibitors. Corticosteroids generally are transported passively into the cytoplasm and bind to intracellular steroid receptors, which are then transported into the nucleus where they exert their effects via gene expression. On the other hand, NSAIDs generally inhibit the activity of cyclooxygenase enzymes while TNF inhibitors typically bind TNF, preventing ligand-receptor binding, suppressing two important inflammatory signaling cascades. However, singularly targeting specific pathological signaling pathways may not reverse the harm from chronic or overactive inflammation alone. The identification of novel strategies to treat overall inflammation or upstream modalities is desirable, and strategies that prevent or reverse underlying pathologies could foster a paradigm shift in how physicians manage inflammation.

An intriguing target for treating chronic inflammatory conditions such as osteoarthritis is a cytosolic, multiprotein complex known as the inflammasome. The inflammasome assembles during inflammation to activate the caspase-1-mediated release of the proinflammatory cytokines interleukin-1beta (IL-1beta) and interleukin 18 (IL-18). Moreover, inflammasome activation generally initiates other inflammatory signaling cascades. Thus, inflammasome inhibitors could potentially quiesce several different inflammatory pathways and even prevent the progression of inflammation. Pharmaceuticals that target inflammasomes are in clinical development (see, for example, Marchetti et al., "OLT1177, β-sulfonyl nitrile compound, safe in humans, inhibits the NLRP3 inflammasome and reverses the metabolic cost of inflammation," PROC. NAT'L ACAD. SCI. U.S.A. 2018; 115(7)). The identification of an inflammasome antagonist that displays efficacy at inhibiting multiple inflammatory signaling pathways nevertheless remains elusive. Such an antagonist would likely provide therapeutic benefits in the treatment of chronic inflammatory diseases including osteoarthritis.

Pain associated with inflammation can be treated directly with analgesics such as opiates, which generally target opioid receptors in the brain. Local analgesics include NSAIDs, capsaicin, and lidocaine. Capsaicin targets vanilloid receptors, and lidocaine targets voltage-gated sodium channels. Additionally, N-methyl-D-aspartate (NMDA) receptor antagonists are known to display analgesic effects, which analgesics include, for example, ketamine and nitrous oxide. NMDA receptor antagonists are not generally prescribed for long-term pain management or to treat pain associated with inflammation.

The NMDA receptor is a glutamate receptor and calcium ion channel. The binding of two glutamates to an NMDA receptor activates the calcium ion channel to increase calcium permeability. Antagonists such as ketamine and nitrous oxide block the calcium channel. NMDA receptor activation can contribute to the development and maintenance of chronic pain conditions by inducing sensitization of pain-sensing neurons, and the NMDA receptor therefore plays a role in synaptic plasticity and pain.

Glutamate, which functions as a neurotransmitter when binding NMDA receptors, is also an amino acid building block of proteins and a precursor and metabolite in numerous other biochemical pathways. Glutamate is notably the transamination product of the citric acid cycle intermediate alpha-ketoglutarate (AKG), and a number of different enzymes interconvert glutamate and AKG.

The citric acid cycle (which is also known as the Krebs cycle) is a series of enzymatic reactions that take place in the mitochondria and generate energy in the form of adenosine triphosphate (ATP). Beta-oxidation of fatty acids breaks down fatty acids to produce acetyl-CoA, which enters the citric acid cycle in the mitochondria to generate ATP. AKG is not directly formed from fatty acids. Fatty acids first undergo beta-oxidation to generate acetyl-CoA, which can be converted to AKG. The enzyme glutamate dehydrogenase can catalyze the conversion of glutamate into AKG and NADPH, which NADPH is involved in cellular processes such as fatty acid synthesis and antioxidant defense. Whether pharmacological manipulation of the citric acid cycle or its intermediates can affect NMDA receptor activation to produce therapeutic effects, for example, by modulating glutamate concentration, remains unknown.

SUMMARY

Various aspects of the disclosure relate to pharmaceutical compositions comprising a hyaluronic acid (HA) hydrogel in combination with a saturated fatty acid (for example, decanoic acid (capric acid), octanoic acid (caprylic acid), and other medium-chain fatty acids). In some embodiments, aspects of the disclosure relate to a pharmaceutical composition comprising a HA hydrogel in combination with a steroid (for example, dexamethasone or esters thereof). In some embodiments, the pharmaceutical composition may be administrable locally, topically, or by injection. In some specific embodiments, the pharmaceutical composition may be administrable by intra-articular injection.

BRIEF DESCRIPTION OF THE DRAWINGS

FIG. 3A depicts human chondrocytes cultured on hyaluronic acid hydrogels that were incubated for four days without decanoic acid, in which small spheroids settled through the gel to the bottom surface of a culture well. FIG. 3B depicts human chondrocyte spheroids that were incubated for four days with decanoic acid; under these conditions, the spheroids generated interconnected networks that suspended the spheroids in a hyaluronic acid hydrogel above the bottom surface of the culture well.

FIG. 4A depicts human chondrocyte cultures that were incubated for 20 days without decanoic acid, in which free cells and spheroids have settled on the bottom surface of a culture well to establish a confluent monolayer. Conversely, FIG. 4B depicts human chondrocyte cultures incubated for 20 days with 1 millimolar decanoic acid resulting in increased condensation and the development of large spheroids that may be representative of enhanced differentiation.

FIG. 6A depicts the viability of resting cells while FIG. 6B depicts the viability of activated cell cultures presented in FIG. 5. Cells treated with 6 millimolar decanoic acid displayed a significant decrease in viability whereas lower concentrations of decanoic acid did not exhibit significant changes in cellular viability relative to vehicle controls.

DETAILED DESCRIPTION

Various aspects of the disclosure relate to a method of enhancing the efficacy of hyaluronic acid (HA) hydrogels, such as Synvisc, by incorporating compounds that can 1) reduce inflammation and inflammasome activity; and 2) promote chondrocyte condensation, redifferentiation, and chondrogenesis.

Inflammasomes are multi-protein complexes that assemble in the cytosol of cells in response to various innate immunological stimuli (for example, pathogen-associated molecular pattern molecules (PAMPs) and damage-associated molecular pattern molecules (DAMPs)).

These pinwheel-like structures serve as a scaffold to dimerize and activate inflammatory proteases known as caspases. Together with other cellular insults (for example, ATP release and potassium efflux), inflammasomes drive the maturation of IL-1beta and GasDermin D. IL-1beta concentration therefore directly correlates with inflammasome activity, and compounds that decrease IL1-beta therefore typically decrease inflammasome activity.

Inflammation contributes to the pathology of osteoarthritis (OA). IL-1beta, for example, promotes synovitis, cartilage loss, osteophyte formation, and the dedifferentiation of chondrocytes. Macrophages are a primary source of IL-1beta. Some aspects of this disclosure relate to compositions that inhibit the release of IL-1beta by macrophages and that also increase collagen production (for example, as measured by Col2a1 expression). Such compositions can advantageously treat OA by reducing inflammation and disease progression and by promoting cartilage development by re-differentiating osteoarthritic chondrocytes into healthy chondrocytes and by restoring lost collagen.

Various aspects of this disclosure relate to a pharmaceutical composition, comprising an HA hydrogel and a saturated fatty acid (for example, a medium-chain fatty acid).

Compositions comprising the fatty acid decanoic acid and hyaluronic acid can advantageously reduce inflammasome-mediated inflammation. Without limiting this disclosure or any patent claim that matures from this disclosure, fatty acids can bind to and inhibit intracellular inflammasomes, which can reduce IL-1beta signaling and corresponding inflammation. Without limiting this disclosure or any patent claim that matures from this disclosure, fatty acids bind to the lipopolysaccharide-binding sites on inflammasome caspase activation and recruitment domains (CARDs), which inhibits inflammasomes. Without limiting this disclosure or any patent claim that matures from this disclosure, fatty acids can also serve as a carbon source for the citric acid cycle, which can increase concentrations of the citric acid cycle intermediate AKG, which AKG improves nitrogen transport and displays antioxidant properties. Without limiting this disclosure or any patent claim that matures from this disclosure, fatty acids also bind a specific locus on the NACHT domain on the NLRP3 inflammasome that possesses ATPase activity to inhibit activation of the NLRP3 inflammasome. Inhibition of the NACHT domain locus, for example, with the small molecule MCC950 is known to inhibit activation of the NLRP3 inflammasome. Without limiting this disclosure or any patent claim that matures from this disclosure, saturated fatty acids can also inhibit the NLRP3 inflammasome by binding its NACHT domain.

Regardless of their precise mechanism of action, the examples provided below suggest that (1) the fatty acid decanoic acid modulates human monocytes and/or macrophages to reduce IL-1beta signaling, and (2) decanoic acid independently modulates human osteoarthritic chondrocytes to promote their re-differentiation. Each of these effects has an independent, favorable impact on osteoarthritis. Similar medium-chain saturated free fatty acids are expected to display similar effects as well as their monoglyceride counterparts.

In some embodiments, the pharmaceutical composition is effective to reduce inflammation, reduce progression of osteoarthritis, and/or re-differentiate osteoarthritic chondrocytes. In some specific embodiments, the hyaluronic acid and the saturated fatty acid are synergistically effective to reduce inflammasome-mediated inflammation. In some specific embodiments, the hyaluronic acid and the saturated fatty acid are synergistically effective to reduce IL-1beta.

In some embodiments, the HA is high molecular weight HA, which has a molecular weight of at least 500 kilodaltons. In some specific embodiments, the HA is high molecular weight HA, which has a molecular weight of at least 1000 kilodaltons. In some very specific embodiments, the HA is high molecular weight HA, which has a molecular weight of at least 5000 kilodaltons. SYNVISC® (Sanofi-Aventis, United States), for example, comprises HA that has an average molecular weight of about 6000 kilodaltons.

In some embodiments, the saturated fatty acid is selected from hexanoic acid (caproic acid, octanoic acid (caprylic acid), decanoic acid (capric acid), dodecanoic acid (lauric acid), tetradecanoic acid (myristic acid), and hexadecanoic acid (palmitic acid). In some specific embodiments, the saturated fatty acid is octanoic acid or decanoic acid. In some very specific embodiments, the saturated fatty acid is decanoic acid.

Figure 6A:
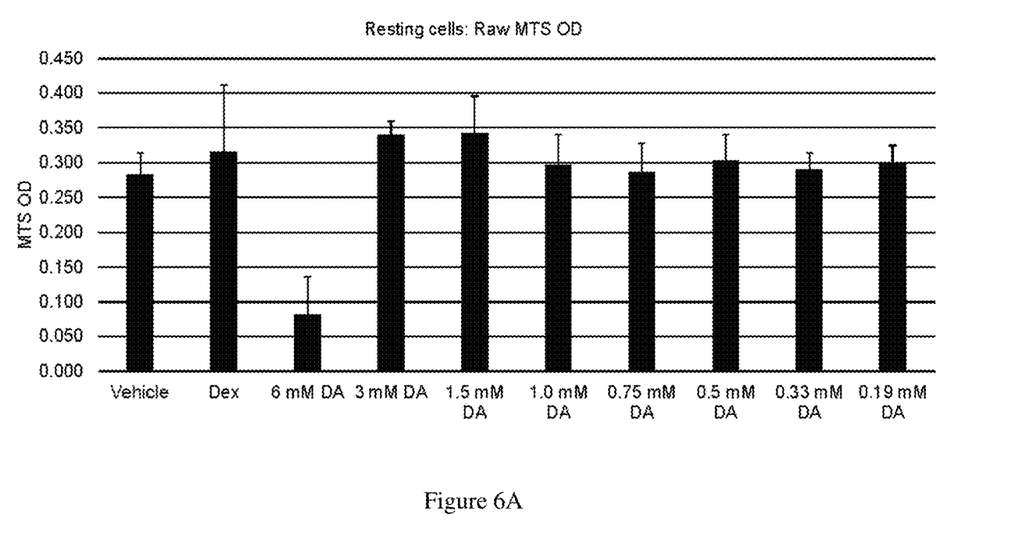
FIGS. 6A and 6B are bar graphs that depict the viability of differentiated THP-1 cells that were differentiated into macrophage-like cells with PMA and then exposed to vehicle, dexamethasone positive control, or decanoic acid at concentrations ranging from 0.19 millimolar to 6 millimolar.
Figure 6B:
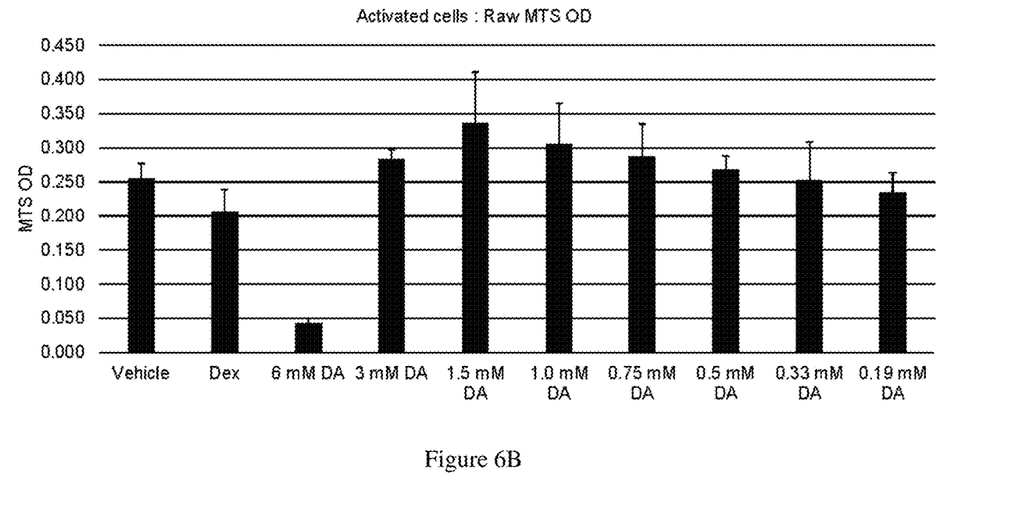

In some embodiments, the pharmaceutical composition comprises the saturated fatty acid at a concentration of at least 10 micromolar and up to 5 millimolar. In some specific embodiments, the pharmaceutical composition comprises the saturated fatty acid at a concentration of at least 10 micromolar and up to 1 millimolar. In some very specific embodiments, the pharmaceutical composition comprises the saturated fatty acid at a concentration of at least 25 micromolar and up to 500 micromolar. Concentrations of either decanoic acid or octanoic acid greater than 5 millimolar are toxic as shown, for example, in FIGS. 6A and 6B.

In some embodiments, the saturated fatty acid has a conjugate base, which is the carboxylate. In some embodiments, the composition comprises a carboxylate, wherein the carboxylate is the conjugate base of the fatty acid. In some embodiments, the fatty acid comprises a conjugate base, which is a carboxylate, and the composition comprises the carboxylate. Decanoic acid, for example, has a pKa (negative log of its acid dissociation constant) of about 4.9, which means that aqueous phases that comprise decanoic acid generally also include its conjugate base decanoate, at least at neutral pH. Various compositions of this disclosure comprise water, and a portion of decanoic acid that dissolves in the water will be deprotonated to form dissolved decanoate. The solubility of decanoic acid in water is about 150 parts per million by mass, and the compositions of this disclosure generally feature concentrations of decanoic acid that are greater than its solubility in water. The concentration of decanoate in the various compositions of this disclosure is therefore less than the concentration that might be determined based on pKa alone.

In some embodiments, the composition comprises a combined concentration of the fatty acid and the carboxylate of at least 300 parts per million and up to 3 percent by mass. In some specific embodiments, the composition comprises a combined concentration of the fatty acid and the carboxylate of at least 1,000 parts per million and up to 1.5 percent by mass. In some even more specific embodiments, the composition comprises a combined concentration of the fatty acid and the carboxylate of at least 1,133 parts per million and up to 1.02 percent by mass. In some very specific embodiments, the composition comprises a combined concentration of the fatty acid and the carboxylate of at least 1,700 parts per million and up to 6,800 parts per million by mass. Lower combined concentrations of a fatty acid and carboxylate display lower efficacy, and higher combined concentrations risk toxicity, which concentration-dependent effects are apparent in light of the exemplification section below and, for example, in FIGS. 5, 6A, and 6B. The therapeutic window for fatty acid concentration is therefore somewhat narrow.

In some embodiments, the composition comprises one or more of sodium cation, potassium cation, and chloride anion. In some specific embodiments, the composition comprises each of sodium cation, potassium cation, and chloride anion.

Various aspects of this disclosure relate to a pharmaceutical composition, comprising an HA hydrogel and a monoglyceride ester of a saturated fatty acid (monoglyceride). At least a portion of free fatty acids get converted into monoglycerides in vivo. Without limiting this disclosure or any patent claim that matures from this disclosure, monoglycerides display activity against inflammation in osteoarthritis. Free fatty acids are converted into monoglycerides in vivo first by acetyl-CoA synthetase, which converts a free fatty acid, coenzyme A (CoA), and ATP into adenosine monophosphate (AMP), pyrophosphate, and a thioester of the free fatty acid and CoA. Monoglyceride acyltransferase then converts the thioester and glycerol into a monoglyceride and CoA.

In some embodiments, the monoglyceride is selected from monohexanoin (monocaproin), monooctanoin (monocaprylin), monodecanoin (monocaprin), monododecanoin (monolaurin), tetradecanoin (monomyristin), and hexadecanoin (monopalmitin). In some specific embodiments, the monoglyceride is selected from monooctanoin and monodecanoin.

In some embodiments, the pharmaceutical composition comprises the monoglyceride at a concentration of at least 10 micromolar and up to 5 millimolar. In some specific embodiments, the pharmaceutical composition comprises the monoglyceride at a concentration of at least 10 micromolar and up to 1 millimolar. In some very specific embodiments, the pharmaceutical composition comprises the monoglyceride at a concentration of at least 25 micromolar and up to 500 micromolar. Without limiting this disclosure or any patent claim that matures from this disclosure, concentrations of either monocaprin or monocaprylin are believed to be toxic at concentrations greater than 5 millimolar based on the toxicity of decanoic acid as shown, for example, in FIGS. 6A and 6B.

Various aspects of this disclosure relate to a pharmaceutical composition, comprising a hyaluronic acid hydrogel and a corticosteroid.

In some embodiments, the pharmaceutical composition is effective to reduce inflammation, reduce progression of osteoarthritis, and/or re-differentiate osteoarthritic chondrocytes. In some specific embodiments, the hyaluronic acid and the corticosteroid are synergistically effective to reduce inflammasome-mediated inflammation. In some specific embodiments, the hyaluronic acid and the corticosteroid are synergistically effective to reduce IL-1beta. In some specific embodiments, the hyaluronic acid and the corticosteroid are synergistically effective to increase Col2a1.

In some embodiments, the corticosteroid is selected from dexamethasone, dexamethasone phosphate, dexamethasone acetate, dexamethasone palmitate, another fatty acid ester of dexamethasone, cortisol, cortisone, triamcinolone, prednisone, prednisolone, methylprednisolone, and betamethasone. In some specific embodiments, the corticosteroid is dexamethasone, dexamethasone phosphate, or dexamethasone acetate. In some specific embodiments, the corticosteroid is a fatty acid ester of dexamethasone such as dexamethasone palmitate. In some very specific embodiments, the corticosteroid is dexamethasone phosphate.

In some embodiments, the pharmaceutical composition comprises at least 1 milligram and up to 10 milligrams of the corticosteroid. In some specific embodiments, the pharmaceutical composition comprises at least 1 milligram and up to 5 milligrams of the corticosteroid. In some very specific embodiments, the pharmaceutical composition comprises at least 2 milligram and up to 5 milligrams of the corticosteroid. A dose of about 3 or 4 milligrams of dexamethasone phosphate, for example, is generally effective at treating osteoarthritis of the knee when administered as an intra-articular injection to the knee.

In some embodiments, the pharmaceutical composition comprises the corticosteroid at a concentration of at least 400 picomolar and up to 20 millimolar.

In some embodiments, the pharmaceutical composition comprises the HA at a concentration of at least 0.01 percent and up to 1 percent.

Various aspects of this disclosure relate to a syringe that contains a pharmaceutical composition as described anywhere else in this disclosure.

Various aspects of this disclosure relate to a method to treat osteoarthritis in a human patient, comprising administering a therapeutically effective amount of the pharmaceutical composition described anywhere in this disclosure to the human patient.

In some embodiments, the administering is local administering in proximity to a joint affected by the osteoarthritis. In some specific embodiments, the administering is selected from topical administering and injecting. In some very specific embodiments, the administering is intra-articular injection.

In some embodiments, the method comprises injecting the pharmaceutical composition into a joint of the patient. In some specific embodiments, the method comprises injecting the pharmaceutical composition into a joint of the patient, wherein the joint is affected by osteoarthritis.

In some embodiments, the joint is selected from the knee, hip, and shoulder. In some specific embodiments, the joint is the knee.

In some embodiments, the method comprises re-injecting a second therapeutically effective amount of the pharmaceutical composition into the joint of the patient 5 to 25 days after the initial injection. In some specific embodiments, the method comprises re-injecting a second therapeutically effective amount of the pharmaceutical composition into the joint of the patient 5 to 15 days after the injecting.

In some embodiments, the pharmaceutical composition is effective to decrease prostaglandin E2 (PGE2) concentration in the patient. In some specific embodiments, the pharmaceutical composition is effective to decrease PGE2 concentration in a joint affected by osteoarthritis in the patient, for example, following injection of the pharmaceutical composition into or adjacent to the joint. In some very specific embodiments, the hyaluronic acid and the saturated fatty acid are synergistically effective to decrease PGE2 concentration in the patient. In some very specific embodiments, the hyaluronic acid and the monoglyceride are synergistically effective to decrease PGE2 concentration in the patient. In some very specific embodiments, the hyaluronic acid and the corticosteroid are synergistically effective to decrease PGE2 concentration in the patient.

In some embodiments, the pharmaceutical composition is effective to decrease inflammasome-mediated inflammation in the patient. In some specific embodiments, the pharmaceutical composition is effective to decrease inflammasome-mediated inflammation in a joint affected by osteoarthritis in the patient, for example, following injection of the pharmaceutical composition into or adjacent to the joint. In some very specific embodiments, the hyaluronic acid and the saturated fatty acid are synergistically effective to decrease inflammasome-mediated inflammation in the patient. In some very specific embodiments, the hyaluronic acid and the monoglyceride are synergistically effective to decrease inflammasome-mediated inflammation in the patient. In some very specific embodiments, the hyaluronic acid and the corticosteroid are synergistically effective to decrease inflammasome-mediated inflammation in the patient.

In some embodiments, the pharmaceutical composition is effective to decrease IL-1beta concentration in the patient. In some specific embodiments, the pharmaceutical composition is effective to decrease IL-1beta concentration in a joint affected by osteoarthritis in the patient, for example, following injection of the pharmaceutical composition into or adjacent to the joint. In some very specific embodiments, the hyaluronic acid and the saturated fatty acid are synergistically effective to decrease IL-1beta concentration in the patient. In some very specific embodiments, the hyaluronic acid and the monoglyceride are synergistically effective to decrease IL-1beta concentration in the patient. In some very specific embodiments, the hyaluronic acid and the corticosteroid are synergistically effective to decrease IL-1beta concentration in the patient.

In some embodiments, the pharmaceutical composition is effective to increase Col2a1 in the patient. In some specific embodiments, the pharmaceutical composition is effective to increase Col2a1 in a joint affected by osteoarthritis in the patient, for example, following injection of the pharmaceutical composition into or adjacent to the joint. In some very specific embodiments, the hyaluronic acid and the saturated fatty acid are synergistically effective to increase Col2a1 in the patient. In some very specific embodiments, the hyaluronic acid and the monoglyceride are synergistically effective to increase Col2a1 in the patient. In some very specific embodiments, the hyaluronic acid and the corticosteroid are synergistically effective to increase Col2a1 in the patient.

In some embodiments, the pharmaceutical composition is effective to inhibit cyclooxygenase in the patient such as COX-1 or COX-2. In some specific embodiments, the pharmaceutical composition is effective to inhibit cyclooxygenase in a joint affected by osteoarthritis in the patient, for example, following injection of the pharmaceutical composition into or adjacent to the joint. In some very specific embodiments, the hyaluronic acid and the saturated fatty acid are synergistically effective to inhibit cyclooxygenase in the patient. In some very specific embodiments, the hyaluronic acid and the monoglyceride are synergistically effective to inhibit cyclooxygenase in the patient. In some very specific embodiments, the hyaluronic acid and the corticosteroid are synergistically effective to inhibit cyclooxygenase in the patient.

In some embodiments, the pharmaceutical composition is effective to re-differentiate osteoarthritic chondrocytes in the patient. In some specific embodiments, the pharmaceutical composition is effective to re-differentiate osteoarthritic chondrocytes in a joint affected by osteoarthritis in the patient, for example, following injection of the pharmaceutical composition into or adjacent to the joint. In some very specific embodiments, the hyaluronic acid and the saturated fatty acid are synergistically effective to re-differentiate osteoarthritic chondrocytes in the patient. In some very specific embodiments, the hyaluronic acid and the monoglyceride are synergistically effective to re-differentiate osteoarthritic chondrocytes in the patient. In some very specific embodiments, the hyaluronic acid and the corticosteroid are synergistically effective to re-differentiate osteoarthritic chondrocytes in the patient.

The following Examples provide a framework to implement various aspects of the disclosure, and these Examples do not limit any aspect of the disclosure or any patent claim that matures from this patent document.

EXEMPLIFICATION

Example 1. The Combination of HA and Decanoic Acid Increases SOX9, ACAN, and Col2a1 Expression in Human Osteoarthritic Chondrocytes Chondrocytes are a cell type unique to articular joints that maintain the structural integrity of cartilage through the production of extracellular matrix proteins. One of the hallmarks of osteoarthritis is an imbalance in the anabolic and catabolic functions of chondrocytes. Repeated mechanical insults and inflammation drive changes in chondrocyte differentiation, resulting in the production of irregular collagen types and proteolytic enzymes.

The process in which chondroprogenitor cells mature to chondrocytes is called chondrogenesis. Growth factors (for example, TGF-β) and transcription factors (for example, SOX9) promote changes in transcriptional programming that induce the production of cartilage. One of the hallmarks of this process is the condensation of these cells into tightly packed nodules or spheroids.

Human osteoarthritic chondrocytes were derived from osteoarthritic tissue and cultured for 24 days in the presence of decanoic acid with medium exchanges performed weekly. The chondrocytes were layered on top of an HA hydrogel (SYNVISC®, Sanofi-Aventis, United States). Following 24 days, the cells were fixed with paraformaldehyde and immunostained for SOX9, Col2a1, and ACAN.

Exposure of high-density monolayers of osteoarthritic chondrocytes to decanoic acid enhanced nuclear staining for SOX9 in a dose-dependent manner for cultures comprising vehicle, 0.1 millimolar decanoic acid, 0.5 millimolar decanoic acid, and 1 millimolar decanoic acid. Cell cultures containing 1 millimolar decanoic acid appeared to exhibit enhanced spheroid development or condensation, and the resulting spheroids also stained strongly for SOX9. The correlation between decanoic acid concentration and SOX9 expression suggests that decanoic acid promotes chondrocyte redifferentiation.

Figure 1:
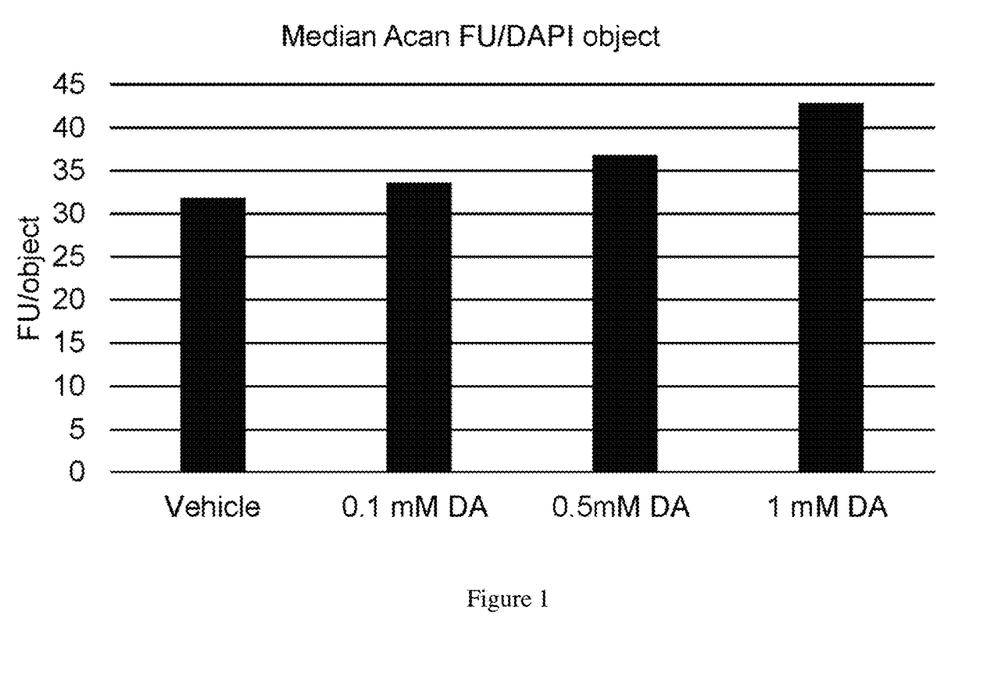
FIG. 1 is a bar graph that depicts a dose-dependent increase in aggrecan (ACAN) immunofluorescence staining (FU) of human osteoarthritic chondrocyte cultures in response to increasing millimolar (mM) concentrations of decanoic acid (DA) as compared to vehicle control. ACAN is an articular cartilage-specific proteoglycan that is important to the proper function and the load-bearing capacity of cartilage. Data is presented as the fluorescence of photographic images captured on an epifluorescent microscope for the ACAN signal (FU) normalized to the signal of 4',6-diamidino-2-phenylindole (DAPI) nuclear stain, designated as FU/DAPI.

Exposure of high-density monolayers of osteoarthritic chondrocytes to decanoic acid resulted in a dose-dependent increase in staining for aggrecan (ACAN) for cultures comprising vehicle, 0.1 millimolar decanoic acid, 0.5 millimolar decanoic acid, and 1 millimolar decanoic acid. Exposure of low-density monolayers of osteoarthritic chondrocytes to decanoic acid also resulted in dose-dependent intracellular staining for ACAN with the strongest staining observed at 1 millimolar decanoic acid (FIG. 1). Furthermore, chondrocyte spheroids on HA hydrogels exhibited strong ACAN immunostaining when exposed to 1 millimolar decanoic acid.

Exposure of high-density monolayers of osteoarthritic chondrocytes to decanoic acid resulted in dose-dependent punctate staining for Col2a1 for cultures comprising vehicle, 0.1 millimolar decanoic acid, 0.5 millimolar decanoic acid, and 1 millimolar decanoic acid with peak staining observed at 0.5 millimolar decanoic acid. Exposure of low-density monolayers of osteoarthritic chondrocytes to decanoic acid resulted in strong punctate immunostaining for Col2a1 for chondrocytes cultured with 1 millimolar decanoic acid as well.

The foregoing results suggest that the combination of high molecular weight HA and decanoic acid is effective at re-differentiating osteoarthritic chondrocytes.

Example 2. The Combination of HA and Decanoic Acid Increases Col2a1 Expression in Human Osteoarthritic Chondrocytes and Promotes Distinct Spheroid Morphologies Human osteoarthritic chondrocytes were derived from osteoarthritic tissue and cultured for 20 days in the presence of decanoic acid with medium exchanges performed every 2-3 days. The chondrocytes were layered on top of an HA hydrogel (SYNVISC®, Sanofi-Aventis, United States). Following 20 days, hyaluronidase was added to release the cells from the hydrogel, the cells were collected, and total RNA was isolated.

Figure 2:
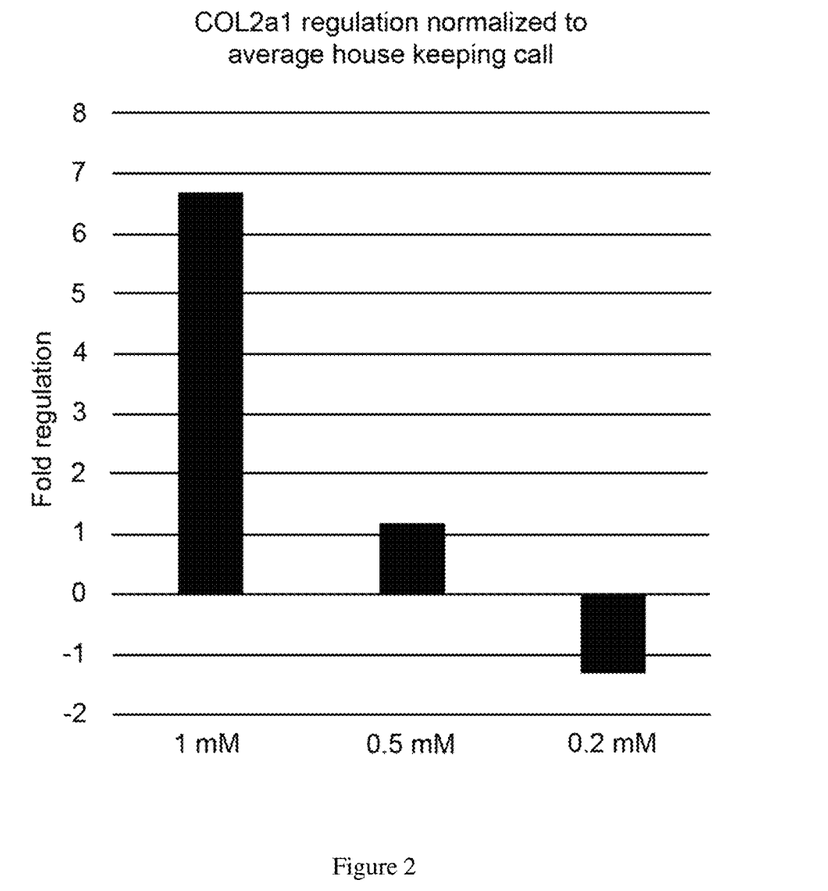
FIG. 2 is a bar graph that depicts a dose-dependent increase in the relative expression of collagen, type II, alpha 1 (Col2a1) in human osteoarthritic chondrocyte cultures in response to increasing millimolar (mM) concentrations of decanoic acid (DA). Col2a1 is a primary component of hyaline cartilage. Data is presented as delta delta relative expression calculations derived from quantitative, real-time reverse transcript-polymerase chain reaction (real-time RT-PCR) amplification calls for Col2a1 mRNA concentrations detected in treatment groups versus vehicle controls and normalized to glyceraldehyde 3-phosphate dehydrogenase (GAPDH), actin, and 18S ribosomal RNA transcripts.

Real-time RT-PCR was performed with delta-delta CT analysis for relative gene expression against GAPDH, actin, and 18S ribosomal RNA transcripts. 0.5 millimolar decanoic acid resulted in a 1-fold increase in Col2a1 mRNA, and 1 millimolar decanoic acid resulted in a 7-fold increase in Col2a1 mRNA (FIG. 2).

Figure 3A:
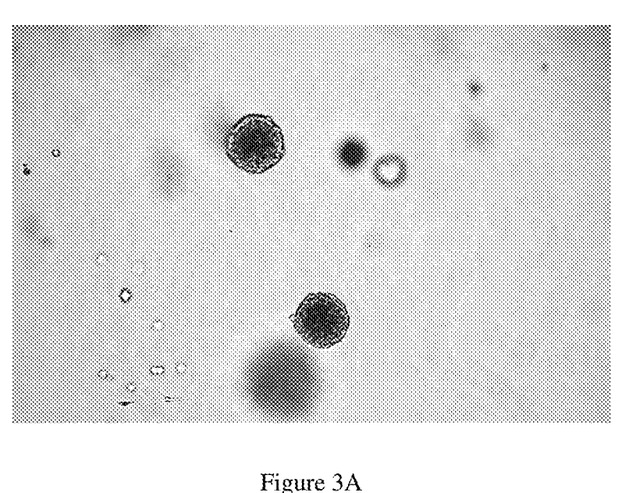
FIGS. 3A and 3B are microscope images of human chondrocyte spheroids following four days of incubation with or without decanoic acid. One of the primary modes of action observed following the treatment of primary human chondrocytes cultured on hyaluronic acid hydrogels with decanoic acid is increased condensation and spheroid formation.
Figure 3B:
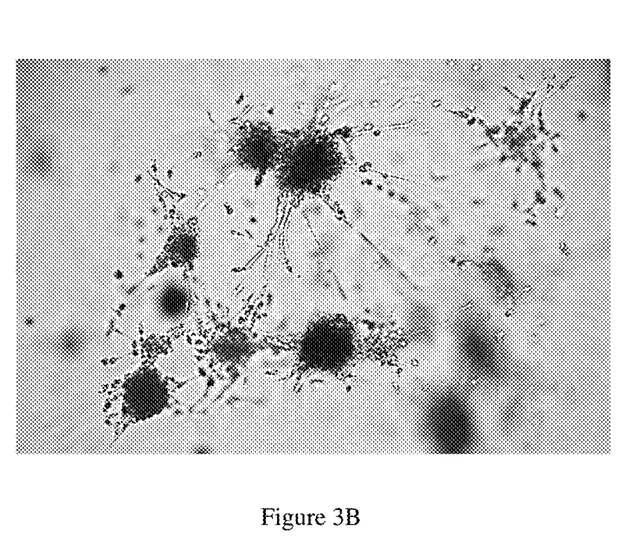

Microscopic examination of these chondrocyte models after 4 days of culture revealed distinct morphological differences in the presence and absence of decanoic acid, which promoted interconnected networks of spheroids. The interconnected networks allowed the chondrocyte spheroids to exist suspended in the HA hydrogel in contrast with the absence of decanoic acid, in which case the spheroids drifted to the surface below the hydrogel (FIGS. 3A & 3B).

Figure 4A:
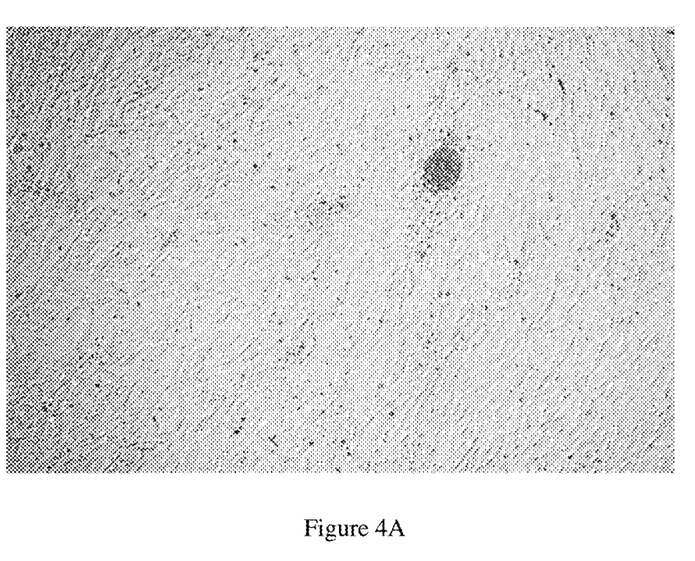
FIGS. 4A and 4B are microscope images of human chondrocyte spheroids following 20 days of incubation with and without decanoic acid.
Figure 4B:
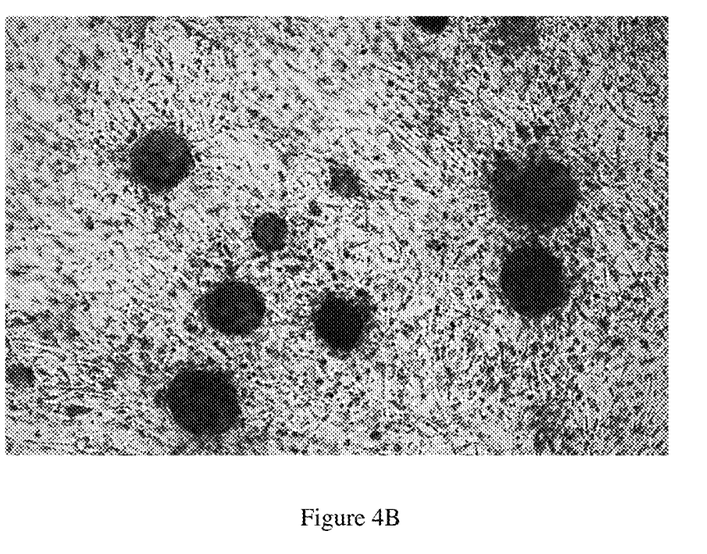

Examination of the chondrocyte spheroids after 20 days of culture revealed additional morphological differences in the presence and absence of decanoic acid. Control chondrocytes established a monolayer on the bottom surface of their culture wells (FIG. 4A). The addition of decanoic acid resulted in large spheroid development or condensation, which is indicative of enhanced differentiation (FIG. 4B).

The foregoing findings suggest that the combination of high molecular weight HA and decanoic acid is effective at re-differentiating osteoarthritic chondrocytes.

Example 3. Decanoic Acid Inhibits IL-1Beta Release from Human Macrophage-Like Cells The human monocyte cell line THP-1 was differentiated into macrophage-like cells with PMA for 72 hours. Following differentiation, the cells were exposed to decanoic acid in 96-well tissue culture plates at 25,000 cells per well at decanoic acid concentrations ranging from 0.2 millimolar to 6 millimolar. Cells were then activated with 100 nanograms per milliliter lipopolysaccharide (LPS) for 24 hours followed by an additional hour with 10 millimolar adenosine triphosphate (ATP). LPS is a toll-like receptor 4 (TLR4) agonist, and ATP activates sodium channels to promote inflammasome activity. The resulting IL-1beta release was quantified by enzyme-linked immunosorbent assay (ELISA).

Figure 5:
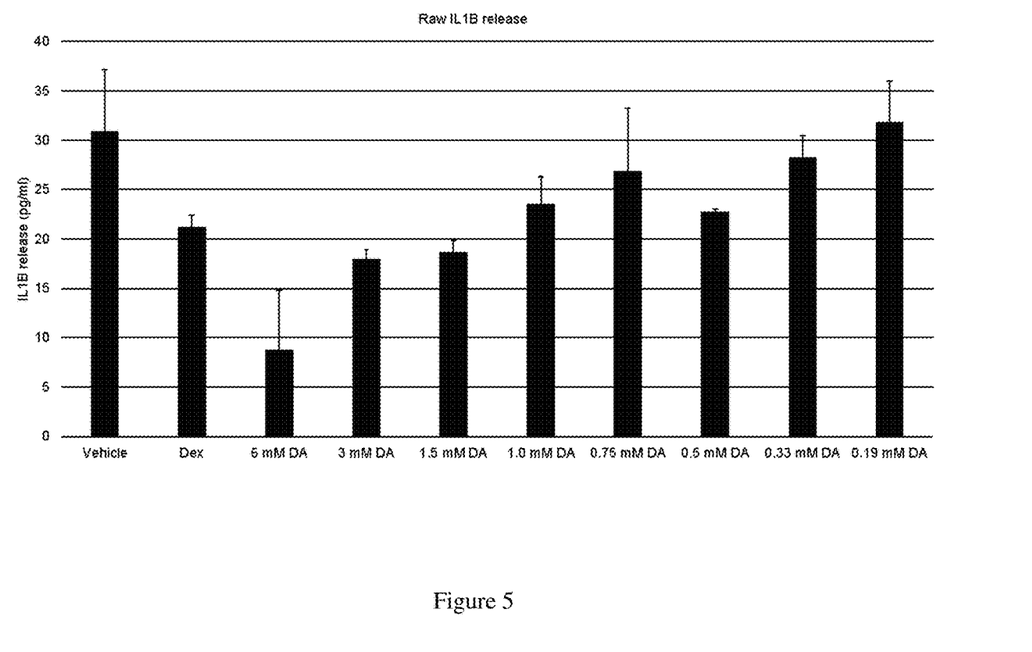
FIG. 5 is a bar graph that depicts concentrations of IL-1beta released from cultures of THP-1 monocyte cells that were differentiated into macrophage-like cells with phorbol 12-myristate 13-acetate (PMA) and then activated with lipopolysaccharide (LPS) followed by an additional incubation with ATP in the presence of vehicle, dexamethasone (Dex) positive control, or decanoic acid at concentrations ranging from 0.19 millimolar to 6 millimolar. The graph displays a dose-dependent inhibition of IL-1beta concentrations in cultures treated with decanoic acid.

Cells cultured with decanoic acid displayed a dose-dependent inhibition of inflammasome-IL-1beta release. 1.5 and 3 millimolar concentrations of decanoic acid displayed superior inhibition relative to the steroid dexamethasone, which was statistically significant (FIG. 5). Resting cells did not release detectable IL-1beta. Then cell density was assessed in both resting and activated cultures using a colorimetric MTS assay with optical density at 490 nanometers (FIGS. 6A & 6B). 6 millimolar decanoic acid displayed an unfavorable effect on cell density, which suggests a narrow therapeutic window for decanoic acid. Furthermore, the viability results indicate that the inhibition of IL-1beta at concentrations at 3 millimolar or below of decanoic acid did not correlate with cell density.

Figure 7:
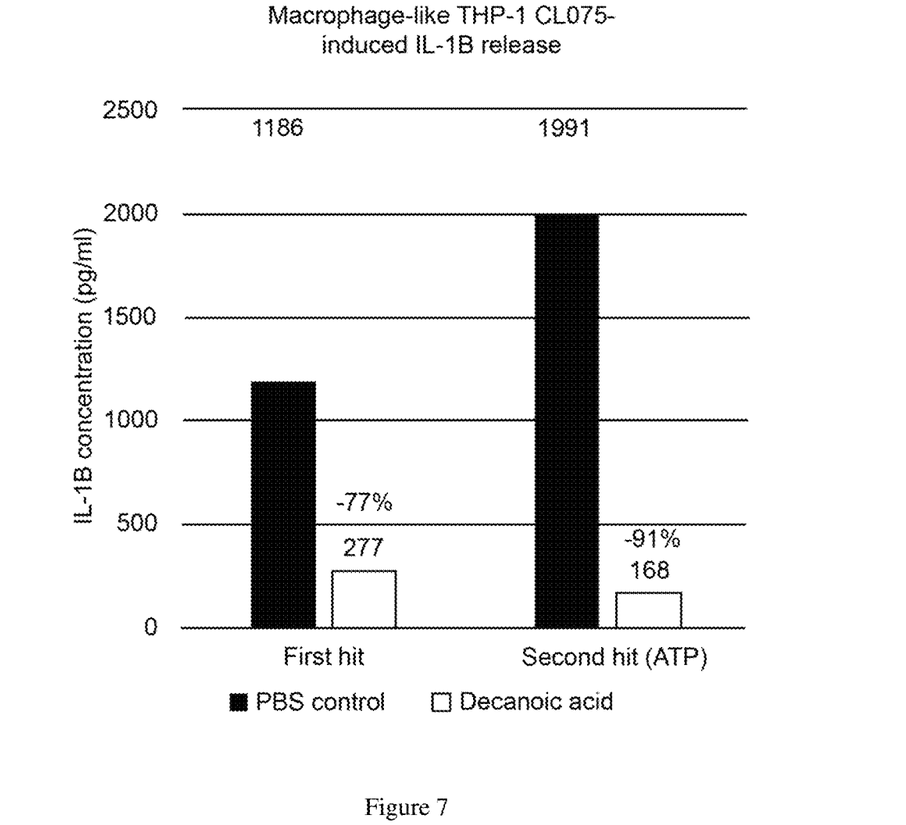
FIG. 7 is a graph that depicts a reduction in IL-1beta concentration for macrophage-like THP-1 cells treated decanoic acid versus a vehicle control following stimulation with both "first hit" CL075 alone or "second hit" CL075 followed by ATP to induce IL-1beta release.

Similar results were observed for activation with the TLR7/8 agonist CL075 instead of LPS. TLR7/8 agonists increase inflammasome activity and IL-1beta release through a different pathway relative to TLR4 agonists. To evaluate this response, THP-1 monocytic cells were differentiated to a macrophage-like state using PMA for 72 hours. Decanoic acid (1 millimolar final concentration) or diluent controls were added, the cells were stimulated with the TLR7/8 agonist CL075, and the cells were incubated for 24 hours at 37 degrees Celsius. To further activate the inflammasome, ATP was then added to the wells designated "second hit," and the cultures were incubated for an additional hour. To indicated wells, hyaluronidase was added for 15 minutes, and all mediums harvested for IL-1beta ELISA quantification. Results are depicted in FIG. 7. The addition of decanoic acid resulted in a 77 percent decrease concentration of IL-1beta in the absence of ATP and a 91 percent decrease following the addition of ATP. Together, these results suggest that decanoic acid can inhibit monocyte- and macrophage-mediated inflammation via different signaling pathways.

Example 4. The Combination of HA and Decanoic Acid Inhibits IL-1Beta Release from Human Macrophage-Like Cells To evaluate in vitro responses of macrophages, THP-1 monocytic cells were differentiated to a macrophage-like state using PMA for 72 hours and then placed on a thin layer of HA hydrogel (SYNVISC®, Sanofi-Aventis, United States) that was then immediately covered with fresh medium. Decanoic acid (1 millimolar final concentrations) or diluent controls were then added, the cells were stimulated with the TLR7/8 agonist CL075, and the cells were incubated for 24 hours at 37 degrees Celsius, and the cultures were incubated for an additional hour with ATP.

Figure 8:
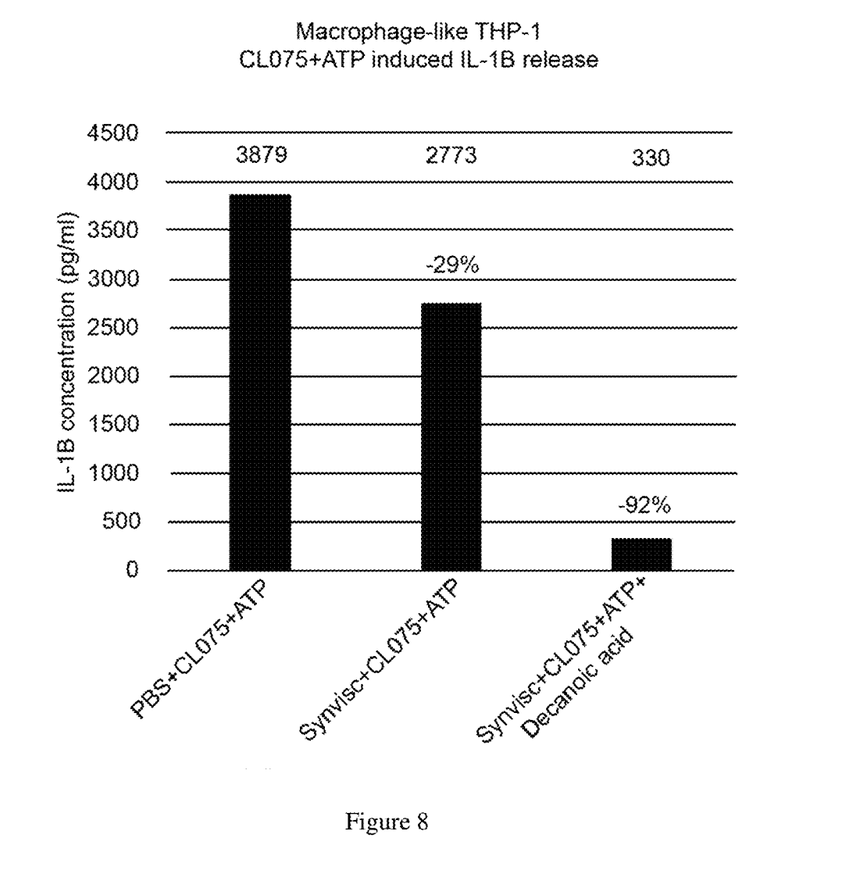
FIG. 8 is a graph that depicts a synergistic reduction in IL-1beta concentration for macrophage-like THP-1 cells treated with hyaluronic acid and decanoic acid versus hyaluronic acid alone following stimulation with CL075 to induce IL-1beta release or both CL075 for 24 hours with a subsequent 1-hour incubation with ATP to induce IL-1beta release. CL075 is a toll-like receptor 7/8 agonist that increases IL-1beta release through an inflammasome-mediated pathway.

The experiment was performed with and without the HA hydrogel to demonstrate the synergy between HA and decanoic acid, and results are reported in FIG. 8. Hyaluronic acid alone resulted in a 29 percent decrease in IL-1beta following CL075 and ATP whereas the combination of hyaluronic acid and decanoic acid resulted in a 92 percent decrease in IL-1beta.

Figure 9:
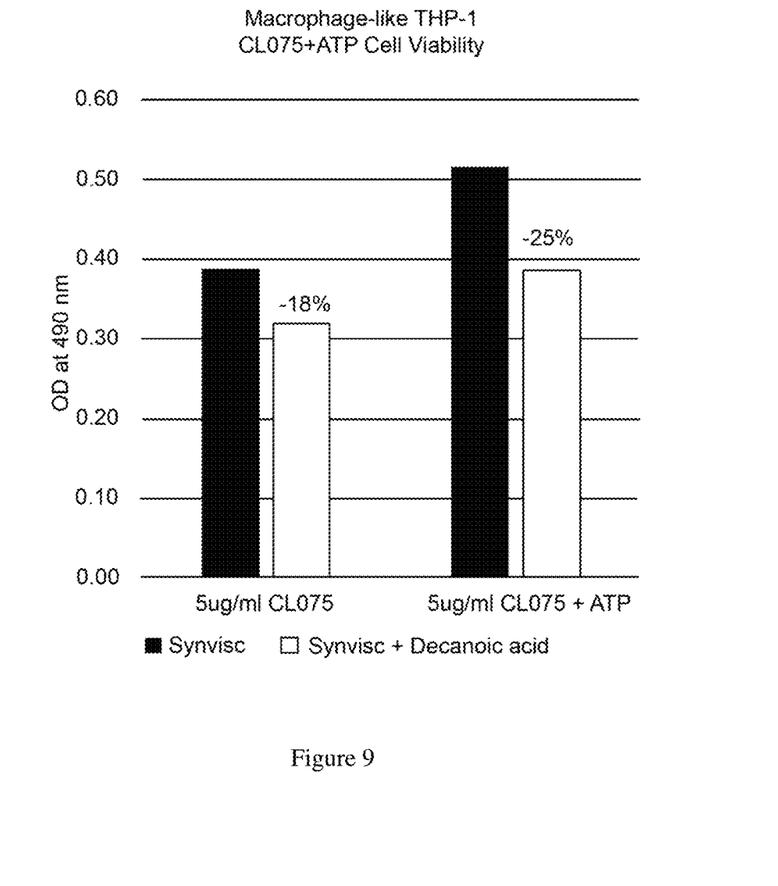
FIG. 9 is a graph that depicts the cellular viability of macrophage-like THP-1 cells treated with hyaluronic acid and decanoic acid versus hyaluronic acid alone following a "first hit model" in which the cells were stimulated with CL075 alone for 24 hours or the "second hit model" presented above where the cells were stimulated with CL075, followed by a 1 hour incubation with 1 mM ATP to induce IL-1β release.

A colorimetric assay confirmed that the inhibition of IL-1beta release was not caused solely by reduced cell counts. Tetrazolium colorimetric dye was added to the cultures at the end of the experiment and cell counts were measured by optical density at 490 nanometers. Optical density decreased by 18 percent upon addition of decanoic acid to a well in the absence of ATP and by 25 percent in the presence of ATP, and these differences are much smaller than the observed reduction in IL-1beta concentration (FIG. 9).

Example 5. The Combination of Hyaluronic Acid and Dexamethasone Synergistically Decreases MMP13 Expression in Osteoarthritic Fibroblast-Like Chondrocytes Osteoarthritic fibroblast-like chondrocytes were cultured for 2 to 28 days in the presence of either 0.1 percent hyaluronic acid, 0.1 micromolar dexamethasone, or both 0.1 percent hyaluronic acid and 0.1 micromolar dexamethasone. Media was exchanged every 2-3 days. Chondrocytes cultured for 2 days, 14 days, or 28 days were analyzed by real time RT-PCR to assess matrix metallopeptidase 13 (MMP13) expression.

MMP13, which is also known as collagenase-3, is an endopeptidase that plays a crucial role in the degradation and remodeling of the extracellular matrix. Under normal physiological conditions, MMP13 is tightly regulated and involved in the turnover of collagen. In osteoarthritis, however, the overexpression and dysregulated activity of MMP13 leads to excessive collagen degradation and cartilage destruction.

Change in MMP13 expression as calculated by delta-delta CT relative to GAPDH expression demonstrated unexpected synergy between 0.1 percent hyaluronic acid and 0.1 micromolar dexamethasone as shown in Table 1 below. The synergy displayed at day 14 displayed a super-additive effect, and the synergy displayed at day 28 was more than an order of magnitude greater than the additive effect. These results suggest that the combination of hyaluronic acid and dexamethasone can synergistically reverse collagen degradation in osteoarthritis.

TABLE 1

Hyaluronic Acid and Dexamethasone Synergistically Decrease MMP13 Expression in Osteoarthritic Fibroblast-Like Chondrocytes

| | Treatment | | |
|---|---|---|---|
| | 0.1 percent hyaluronic acid | 0.1 micromolar dexamethasone | Both 0.1 percent hyaluronic acid and 0.1 micromolar dexamethasone |
| Change in MMP13 expression at day 2 | −4 | 0 | 0 |
| Change in MMP13 expression at day 14 | −2 | −399 | −474 |
| Change in MMP13 expression at day 28 | 1 | −4 | −164 |

What is claimed is:

1. A method to treat osteoarthritis in a human patient, comprising administering a therapeutically effective amount of a pharmaceutical composition to the patient, the pharmaceutical composition consisting of: a hyaluronic acid (HA) hydrogel comprising HA that has a molecular weight of at least 500 kilodaltons, wherein the HA is at a concentration of 0.1 percent; water; and dexamethasone, wherein the dexamethasone is at a concentration of 0.1 micromolar.

2. The method of claim 1, comprising injecting the pharmaceutical composition into a joint of the patient.

3. The method of claim 1, wherein the dexamethasone comprises dexamethasone palmitate.

4. The method of claim 1, wherein the dexamethasone comprises dexamethasone phosphate.

5. The method of claim 1, wherein the dexamethasone comprises dexamethasone acetate.

6. The method of claim 1, wherein the HA and the dexamethasone are synergistically effective to decrease MMP13 expression.

7. A method to treat osteoarthritis in a human patient, comprising administering a therapeutically effective amount of a pharmaceutical composition to the patient, the pharmaceutical composition comprising: a hyaluronic acid (HA) hydrogel comprising HA that has a molecular weight of at least 5,000 kilodaltons, wherein the HA at a concentration of 0.1 percent; water; and
dexamethasone, wherein the dexamethasone is at a concentration of approximately 0.1 micromolar.

8. The method of claim 7, comprising injecting the pharmaceutical composition into a joint of the patient.

9. The method of claim 7, wherein the dexamethasone comprises dexamethasone palmitate.

10. The method of claim 7, wherein the method comprises administering a first amount of the pharmaceutical composition and administering a second amount of the pharmaceutical composition at least 14 days after administering the first amount of the pharmaceutical composition.

11. The method of claim 7, wherein the method comprises administering a first amount of the pharmaceutical composition and administering a second amount of the pharmaceutical composition at least 28 days after administering the first amount of the pharmaceutical composition.

12. The method of claim 7, wherein the HA and the dexamethasone are synergistically effective to decrease MMP13 expression.

* * * * *